United States Patent
Pretre et al.

(10) Patent No.: US 10,371,678 B2
(45) Date of Patent: Aug. 6, 2019

(54) METHOD AND MEASURING APPARATUS FOR DETERMINING GAS PROPERTIES BY CORRELATION

(71) Applicant: MEMS AG, Brugg (CH)

(72) Inventors: Philippe Pretre, Dattwil (CH); Andreas Kempe, Zurich (CH)

(73) Assignee: MEMS AG, Brugg (CH)

( * ) Notice: Subject to any disclaimer, the term of this patent is extended or adjusted under 35 U.S.C. 154(b) by 363 days.

(21) Appl. No.: 15/379,003

(22) Filed: Dec. 14, 2016

(65) Prior Publication Data
US 2017/0176402 A1    Jun. 22, 2017

(30) Foreign Application Priority Data
Dec. 19, 2015    (EP) ................... 15003639

(51) Int. Cl.
| G06F 19/00 | (2018.01) |
| G01N 33/00 | (2006.01) |
| G01F 15/02 | (2006.01) |
| G01F 1/74 | (2006.01) |
| G01N 33/22 | (2006.01) |

(52) U.S. Cl.
CPC .......... *G01N 33/0004* (2013.01); *G01F 1/74* (2013.01); *G01F 15/022* (2013.01); *G01F 15/024* (2013.01); *G01N 33/225* (2013.01)

(58) Field of Classification Search
CPC ........ G01F 15/022; G01F 15/024; G01F 1/74; G01F 1/8431
USPC .................... 702/24, 25, 182–185
See application file for complete search history.

(56) References Cited

U.S. PATENT DOCUMENTS

| 6,124,931 A * | 9/2000 | Hill ................ G01B 9/02007 356/484 |
| 7,364,697 B2 * | 4/2008 | McFarland .......... B01J 19/0046 250/341.1 |
| 2006/0228261 A1 * | 10/2006 | Iwamoto ................ B01J 20/28 422/88 |

FOREIGN PATENT DOCUMENTS

| DE | 19921167 | 8/2000 |
| EP | 0715169 | 6/1996 |
| EP | 0939317 | 9/1999 |
| EP | 2015056 | 1/2009 |
| EP | 2806271 | 11/2014 |

OTHER PUBLICATIONS

European Search Report cited in EP 15 00 3639 dated Mar. 24, 2016, two pages.

* cited by examiner

Primary Examiner — Edward Raymond
(74) Attorney, Agent, or Firm — Nixon & Vanderhye P.C.

(57) ABSTRACT

A method in which a gas property (Q) is determined by correlation from physical measuring quantities ($\mu_j$) of the gas mixtures. In the method, the physical measuring quantities are combined into a sensor output ($S_{out}$) by making use of a sensor output function ($f$), wherein the sensor output function is determined in such a way that a group of gas mixtures can be separated from a set of gas mixtures for which the gas property (Q) is determined, within which the correlation between the sensor output ($S_{out}$) and the desired gas property (Q) is better than in the entire set.

16 Claims, 13 Drawing Sheets

METHOD AND MEASURING APPARATUS FOR DETERMINING GAS PROPERTIES BY CORRELATION

RELATED APPLICATION

This application claims priority to European Patent Application 15003639.0 filed Dec. 19, 2015, which is incorporated by reference in its entirety.

BACKGROUND

The invention relates to a method and a measuring apparatus for determining gas properties by correlation.

The (natural) gas composition and thus the gas quality will fluctuate in future to a higher extent and more frequently than today as a result of new sources of origin (biogas, liquefied natural gas from all areas of the world, hydrogen from the exploitation of excess current in alternative power generation) and will therefore have different effects in gas application processes, which may also include such that have a negative effect. With knowledge of the relevant gas properties on site, the processes could be adjusted to the varying gas quality in order to ensure optimal and secure operation. In connection with gas properties that are relevant in this context, this includes for example the Wobbe index for burner controllers, the air to fuel ratio in power generation plants such as industrial furnaces and fuel cells, the methane number for gas motors, or the calorific value for billing the purchased energy quantity. These gas properties can often only be measured directly at great expense, so that an on-site determination is usually not economical.

A method and a measuring apparatus for determining physical gas properties is known from European Patent Application EP 2 806 271 A1, in which a desired gas property is determined by means of correlation from several basic physical quantities of a gas that can be determined in a simple manner such as the thermal conductivity. An on-site determination of the desired gas property is then also enabled with this simple measuring apparatus. Although a potential correlation function is mentioned in equation 16 of the mentioned patent application, the precision which applies to this correlation for the gas mixture shown in FIG. 4 is not stated.

SUMMARY OF THE INVENTION

Depending on the gas property and the selection of gas mixtures for which the gas property is to be determined, it may be difficult to determine the desired gas property with sufficient precision from the measuring quantities with only one correlation.

It is therefore an exemplary application of the invention to provide a method and a measuring apparatus with which the correlation of gas properties can be improved and/or the selection of gas mixtures for which the correlation provides a desired precision can be increased.

The present method is based on the observation of the applicant that within a set of gas mixtures for which a gas property is to be determined there are groups in which the gas mixtures have a physically similar behaviour. In the context of the determination of gas properties this means that the correlation between the measured quantities and the desired gas property is better within such a gas mixture group than in the entire set, and that the gas mixtures of such a group can be separated from the remaining gas mixtures of the set by means of physical measuring quantities which are detected in the course of the method.

A connection can be established between the physically similar behaviour of the gas mixtures of a gas mixture group and the similarity in the composition of the gas mixtures. Consequently, the gas mixtures of type $CH_4+H_2$ from one of the embodiments described below form a gas mixture group. The similarity of the composition is however no precondition for the present method. It is merely relevant in this context that the correlation within a gas mixture group is better than in the entire set, and that the gas mixtures of a gas mixture group can be separated from the gas mixtures of the set.

In the method that will be presented below, the correlation is described by a correlation function $f_{corr}$ for the gas property Q, wherein $f_{corr}$ is a function of the sensor output $S_{out}$ $$Q = f_{corr}(\text{sensor output}) := f_{corr}(S_{out}). \quad (1)$$

The method is based on a step-by-step or sectional procedure in which it is attempted to define the sensor output $S_{out,1}$ in a first step in such a way that a first group of gas mixtures from a set can be separated along the $S_{out,1}$ axis from all other gas mixtures of the set and can be correlated with a first correlation function $f_{corr,1}$ so as not to be considered anymore in the next step. The remaining or other gas mixtures of the set are then compared in a second step with a second sensor output $S_{out,2}$ to be newly defined in order to separately correlate a second gas mixture group with a second correlation function $f_{corr,2}$. The procedure can be repeated as often as desired until the desired degree of correlation quality has been reached.

The $i^{th}$ sensor output $S_{out,i}$ (i=1, ..., n) is a function $f_i$ of one or several physical measuring quantities $\mu_j$ (j=1, ..., m) of one or several sensors:

$$S_{out,i} = f_i(\mu_1, \ldots, \mu_m). \quad (2)$$

The correlation function $f_{corr,i}$ (i=1 ... n) can be sectionally different relating to $S_{out,i}$, and even a discontinuous change of $f_{corr,i}$ is possible at the sectional boundaries.

It is a typical aspect in this method that it is possible by introducing the sensor output $S_{out,i}$, which is a function of physical measuring quantities, to make a specific selection for the functions $f_i$ on the basis of tabulated values of these physical measuring quantities for groups of gas mixtures, in particular for given gas mixture groups, which then leads to gas mixture group separation, as described above. If the gas property Q on the Y axis is entered against $S_{out,i}$ on the X axis, the points of the gas mixture exclusively move parallel to the X axis under changing function $f_i$, which considerably facilitates the visual tracking of the effects of the change in the function $f_i$ (see FIG. 1b).

The visual tracking can also be automated by a computer program as follows: the functional parameters $p_{fi}$ of $f_i$, such as polynomial coefficients, exponents or constants, are varied for each function $f_i$ in a set of possible sensor output functions within limit values for $p_{fi}$ to be entered, e.g. by means of a Monte Carlo selection procedure. At the same time, the number of ambiguities is counted, i.e. the number of events for which two or more gas mixtures show "different" values for the quantity Q to be determined at "identical" sensor output $S_{out,i}$. "Identical" and "different" can also mean inside or outside of value intervals to be preset. FIG. 2a shows a possible value for the interval width Δ of the sensor output $S_{out,2}$ for example. It is the object for example to determine the function $f_i$ and the function parameter set $p_{fi}$ in which the lowest number of such ambiguity events occur. If a histogram of these events is produced along the X axis ($S_{out,i}$), such sections can be determined along the X axis, as shown in FIG. 2b, where and for which gas mixture groups a good or better correlation is possible (with a minimum number n of such ambiguity events or minimal variance 3σ of the Q values in case of ambiguity events in an interval). Instead of the minimum search, it is also possible for the selection method to predetermine the maximum permitted number n of ambiguity events or the maximum allowed variance 3σ of the Q values in case of ambiguity events in an interval.

With the present method for determining gas properties, a physical definition of a gas mixture group is also implicitly provided: gas mixtures which are physically similar can be separated from gas mixtures which can also be physically similar among each other but which differ in one physical parameter of similarity from the first gas mixture group.

The thermal degrees of freedom of gas molecules are mentioned as an example for a physical parameter of similarity. According to the equipartition theorem, the same mean energy ½kT is allocated to each degree of freedom in thermal equilibrium. Combustible gases such as methane, ethane and all other higher hydrocarbons act like higher-atom gases with six degrees of freedom, whereas inert gas components such as nitrogen, oxygen and argon can rather be associated with single-atom gases with five degrees of freedom, because specific degrees of freedom are still "frozen" at room temperature. This fact has an effect on the heat capacity of these molecules (more degrees of freedom=higher heat capacity). At the same time, which is chemically caused however, the inert molecules do not contribute to the calorific value (Q). In this case, the gas group with high calorific value (H gases) can therefore be separated from those with low calorific value (L gases) by the measurement of the heat capacity $c_p=\mu$.

Further examples for physical measuring quantities $\mu_i$ are the density ρ, the thermal conductivity λ, the sound velocity $c_s$, the dielectric permittivity ε etc.

Examples for the gas property Q to be determined are the viscosity (which is important in the configuration of pipeline systems), the compression factor Z (which is important for billing purposes in gas transport lines), and also the flame velocity (for thermal applications in the process industry), or direct process parameters such as the ignition angle in gas motors. The latter ones are of particular interest because in this case the physical parameters of similarity are difficult to detect on the basis of the gas composition, since gas properties in the "traditional" sense are given by the gas, whereas the process parameters are given by the process.

In the method for determining gas properties according to the present invention, a gas property to be determined such as a physical gas property is determined by correlation from physical measuring quantities of the gases and/or gas mixtures, wherein the physical measuring quantities are combined into a sensor output by making use of a sensor output function, and the sensor output is compared with a limit value $S_{out}^{sep}$ in order to determine whether the sensor output within the set G of gases and/or gas mixtures to which the method is applied belongs to a group of gases and/or gas mixtures, which are mentioned below as the gas mixture group GG, in which the correlation between the sensor output and the gas property to be determined is better than in the entire set G. If the sensor output belongs to the aforementioned gas mixture group GG, the gas property is determined from the sensor output with a correlation function which is specific to the gas mixture group.

In an advantageous embodiment of the method, the affiliation with a gas mixture group is checked in two, three, four or more steps, in that the physical measuring quantities are combined into a further sensor output respectively by making use of a sensor output function which is specific to the gases and/or gas mixtures $G_{rest,i}$ of the set which remain after the separation of the preceding gas mixture group or groups, which are mentioned below as remaining gases and/or gas mixtures $G_{rest,i}$, and the further sensor output is compared with a further limit value $S_{out,i}^{sep}$ in order to determine whether the further sensor output within the remaining gases and/or gas mixtures $G_{rest,i}$ belongs to a further gas mixture group $GG_i$ in which the correlation between the further sensor output and the gas property to be determined is better than within the remaining gases and/or gas mixtures $G_{rest,i}$. If the further sensor output belongs to the aforementioned further gas mixture group GG the gas property is determined from the further sensor output with a correlation function which is specific to the further gas mixture group.

If the sensor output does not belong to one of the aforementioned gas mixture groups, the gas property can be determined from the sensor output with a correlation function which is specific to the remaining gases and/or gas mixtures.

It may be advantageous in a number of cases to change the sensor output prior to the correlation with a further sensor output function in order to prepare or improve the correlation between the sensor output and the gas property and/or in order to simplify the search for a suitable correlation function.

In a further advantageous embodiment of the method, the sensor output function and a limit value $S_{out}^{sep}$ for the sensor output are determined in such a way that a gas mixture group GG is separated by the limit value from a set G of gases and/or gas mixtures for which the gas property is determined, within which the correlation between the sensor output and the desired gas property is better than in the entire set G.

The separation of gas mixture groups can also occur in two, three, four or more steps in that a new set is respectively formed from the remaining gases and/or gas mixtures $G_{rest,i}$, i.e. from those that have remained from the preceding separation, from which set a further gas mixture group with a separate sensor output function and with a separate limit value $S_{out,i}^{sep}$ for the sensor output is separated, and in that the correlation from the sensor output occurs for the gases and/or gas mixtures of the further gas mixture group with a separate correlation function.

The relationship $S_{out}^{GG} < S_{out}^{sep}$ typically applies to the gases and/or gas mixtures of the gas mixture group GG, and the relationship $S_{out}^{G_{rest}} \geq S_{out}^{sep}$ for the remaining gases and/or gas mixtures $G_{rest}$ of the set, or from case to case, instead of the aforementioned relationships, the relationships $S_{out}^{GG} > S_{out}^{sep}$ and $S_{out}^{G_{rest}} \leq S_{out}^{sep}$ apply.

The method can be carried out automatically irrespective of the aforementioned embodiments and variants, e.g. in a measuring apparatus.

The sensor output function or sensor output functions and/or the limit value or values $S_{out}^{sep}$, $S_{out,i}^{sep}$ for the sensor output and/or the correlation functions are advantageously determined in advance, i.e. typically before the determination of gas properties on site, e.g. on the basis of values of the physical measuring quantities and the gas property to be determined from tables and/or technical literature and/or databases and/or measurements, and are stored as required.

In a further advantageous embodiment of the method, the sensor output function or sensor output functions and/or the limit value or values $S_{out}^{sep}$, $S_{out,i}^{sep}$ for the sensor output are determined by a computer program, in that for each function $f_i$ in a set of possible sensor output functions the respective functional parameters $p_{fi}$ of $f_i$, such as polynomial coefficients, exponents or constants, are varied within preset limit values for $p_{fi}$, e.g. by means of a Monte Carlo selection procedure. The sensor output range is subdivided in this method into intervals and the number of ambiguities is counted in particular in each interval, i.e. the number of events for which two or more gas mixtures show different values for the quantity Q to be determined or the values for the quantity Q to be determined lie outside of a preset value interval. It is the object to determine the function $f_i$ and the respective functional parameter set $p_{fi}$ in which the fewest of such ambiguity events occur, or the variance $3\sigma$ of the values for the quantity Q to be determined is minimal in case of ambiguity events in an interval, or a preset maximum permitted number $n_{max}$ of the ambiguity events or a preset maximum permitted variance $3\sigma_{max}$ of the Q values in case of ambiguity events in an interval is not exceeded.

It is appropriately further determined from which limit value $S_{out,i}^{sep}$ a number $n_{max}$ of the ambiguity events, which is preset per interval for the determination of the limit value or a variance $3\sigma_{max}$ of the Q values which is preset per interval for determining the limit value, is not exceeded in case of ambiguity events.

At least two or all sensor output functions typically differ from each other and/or at least two or all limit values for the sensor output differ from each other.

The points of the gases and/or gas mixtures of the gas mixture group or groups advantageously each lie on a line described by a distinct correlation function or in tolerance ranges which adjoin such a line on both sides and which are e.g. not greater than 0.25% or 0.75% or 2% of the value of the gas property (Q). At least two or all correlation functions typically differ from each other.

In an advantageous embodiment, the sensor output function or sensor output functions are of the type $$S_{out,i} = \mu_1^{p_{1,i}} \cdot \ldots \cdot \mu_m^{p_{m,i}}$$

and $p_{1,i}, \ldots, p_{m,i}$ exponents, and/or the correlation function or correlation functions of the type $$Q = f_{corr,i}(S_{out,i}) = a_{0,i} + a_{1,i} \cdot S_{out,i} + a_{2,i} \cdot S_{out,i}^2$$

and $a_{0,i}$, $a_{1,i}$ and $a_{2,i}$ constants.

The Pearson correlation coefficient can for example be used as a measure for the precision of the correlation, wherein a better correlation means that the Pearson correlation coefficient lies closer to the value +1 or −1, and the absolute value of the difference to the value +1 or −1 is e.g. less than 0.3 or 0.2 or 0.1.

The Pearson correlation coefficient $$Kor(S_{out}, f_{corr}) = \frac{\sum_{k=1}^{n}(S_{out,k} - \overline{S}_{out})(f_{corr,k} - \overline{f}_{corr})}{\sqrt{\sum_{k=1}^{n}(S_{out,k} - \overline{S}_{out})^2 \cdot (f_{corr,k} - \overline{f}_{corr})^2}} \quad (3)$$

is a measure for the deviation of the two variables $S_{out}$, $f_{corr}$ from linearity, wherein $$\overline{S}_{out} = \frac{1}{n}\sum_{k=1}^{n} S_{out,k} \text{ and } \overline{f}_{corr} = \frac{1}{n}\sum_{k=1}^{n} f_{corr,k}$$

are the mean values over all n gases and gas mixtures.

If all n points of the gases and gas mixtures lie on a straight line with a positive gradient, the Pearson correlation coefficient has the value +1. If on the other hand all n points are on a straight line with negative gradient, the value is −1. If all n points are distributed stochastically around a point, there is no correlation and the Pearson correlation coefficient has the value of 0.

The correlation functions which are used in the aforementioned method and in the described embodiments and variants are usually not linear, i.e. the values +1 and −1 of the Pearson correlation coefficient are not reached in most cases. Since the deviations from linearity are moderate in most cases, the Pearson correlation coefficient is very suitable in practice for comparison purposes in that the correlation or correlation function is the better and more precise between the variables $S_{out}$, $f_{corr}$ the closer the Pearson correlation coefficient is to the value +1 or −1.

The physical measuring quantities are advantageously detected by one or several sensors. At least two of the following measuring quantities are detected for example as physical measuring quantities: thermal conductivity, heat capacity, thermal diffusivity, density, flow velocity, mass flow, sound velocity, dielectric constant, viscosity, infrared absorption, pressure and temperature, wherein this list is not exhaustive.

The invention further comprises a measuring apparatus for determining gas properties with one or several sensors for detecting physical measuring quantities and with an evaluation unit which is set up for carrying out a method according to one or several of the embodiments and variants that are described above.

The evaluation unit can form an assembly together with the sensor or sensors for example, or the evaluation unit is formed in a separate or superordinate computing unit.

The method and the measuring apparatus according to the present invention for determining gas properties offer the advantage that as a result of correlation in several steps the precision of the determination of gas properties from measured physical quantities of the gases and/or gas mixtures can be improved, and the quantity of the gases and/or gas mixtures for which the method can be applied with the desired precision is greater than in the case of simple correlation methods. As a result of correlation in several steps, gas mixtures with compositions can also be included in the method for which a determination of gas properties could only be carried out until now at great cost or without the necessary precision.

SUMMARY OF THE DRAWINGS

The invention will be explained below in closer detail by reference to the drawings wherein:

FIG. 2b shows an example of an ambiguity histogram and the expected correlation error for a computer-based selection method for determining the sensor output function in the embodiment shown in FIG. 2a;

DETAILED DESCRIPTION OF THE INVENTION

Methane (G20) is used in all representations shown in FIGS. 1a to 10 as the reference as follows:

$$\mu_i := \mu_{i,Gas}/\mu_{i,CH_4}$$

for all measuring quantities $\mu_i$ in equation (2) and all following paragraphs.

A first embodiment of the method according to the present invention for the correlation of the compression factor Z is described below by reference to FIGS. 1a to 5.

The method is based on a selection or set of gases and/or gas mixtures for which a gas property Q is to be determined.

Figure 1A:
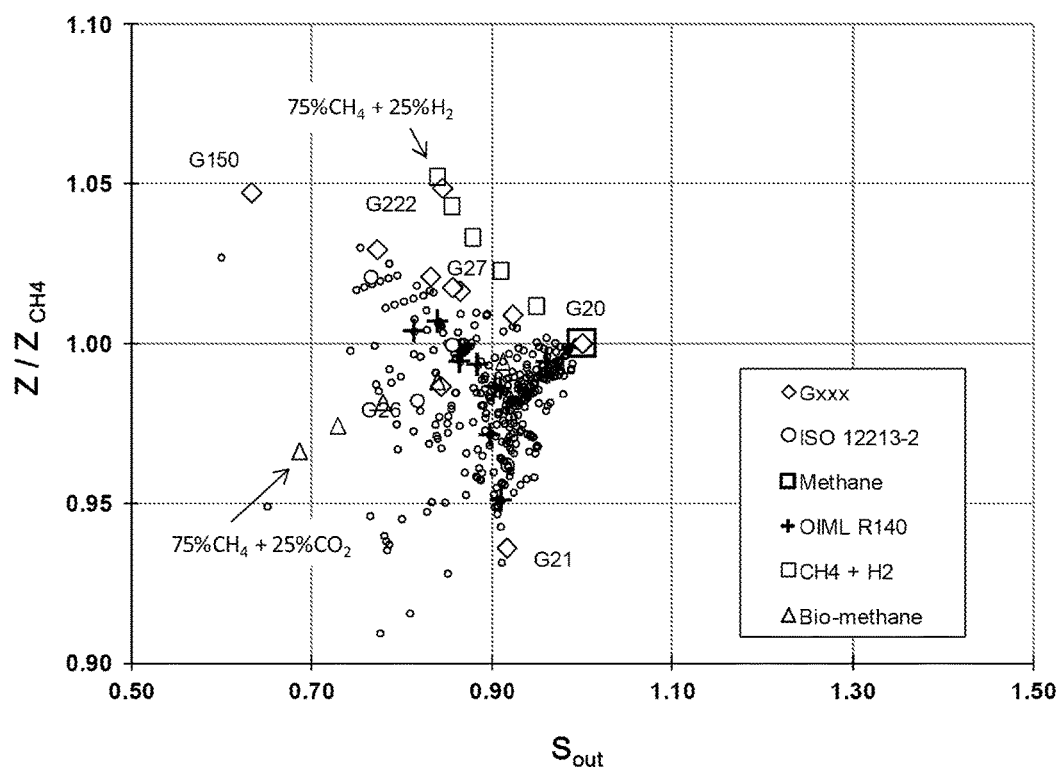
FIG. 1a shows a first embodiment with a graphic representation of the correlation of the compression factor Z according to a method in accordance with the present invention.

It is attempted at first to select the sensor output function $S_{out}$ in such a way that the sensor output can be mapped in an unambiguous manner to the gas property Q for gases and/or gas mixtures of the set, i.e. to the compression factor Z in the first embodiment, e.g. as shown in FIG. 1a by means of the sensor output function $$S_{out} = f(c_p, c_s, \lambda) = c_p^1 \cdot c_s^1 \cdot \lambda^{-1}.$$

Figure 1B:
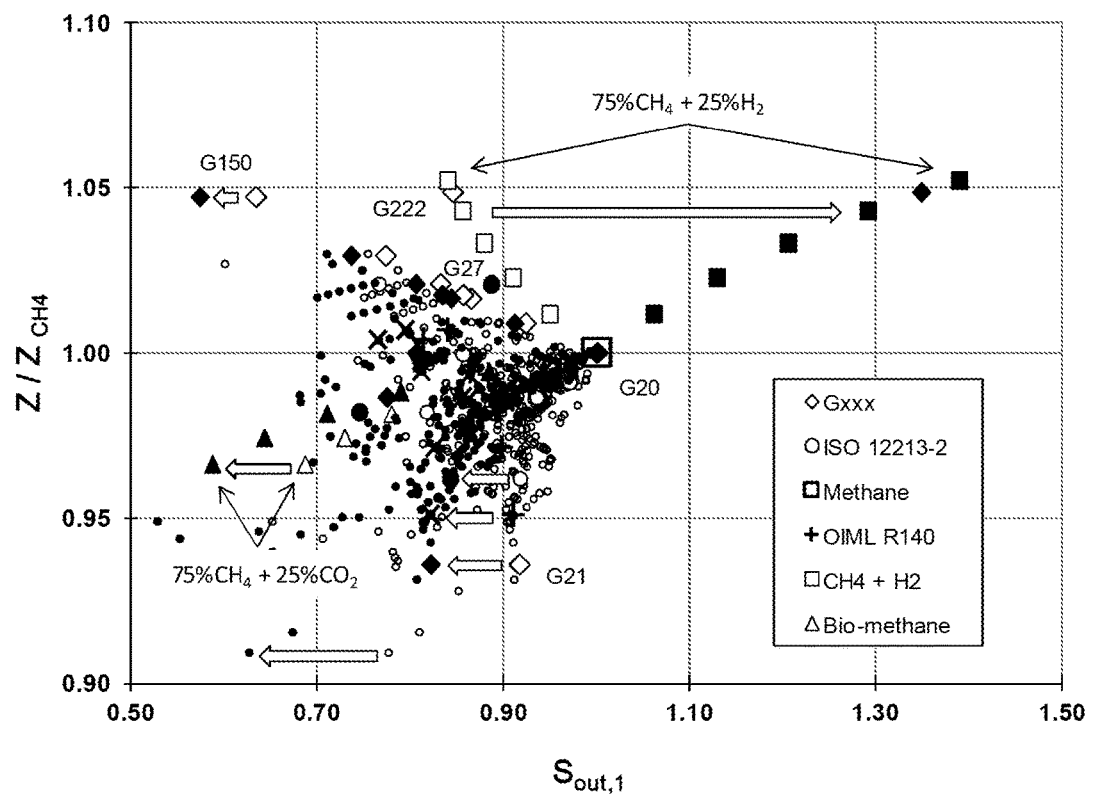
FIG. 1b shows an example for the mutual horizontal displacement of the points of the individual gas mixtures as a result of the change in the sensor output function in the first embodiment.

This means in a graphic representation of Q depending on $S_{out}$ that the points of the gases and/or gas mixtures lie on a line or at least approximately on a line which can be described by a distinct function. If this is not simultaneously possible, as shown in FIG. 1a, for all gases and/or gas mixtures of the set, it is possible to track visually by changing the sensor output function $S_{out,1}$ how the points of the gases and/or gas mixtures are displaced relative to each other. FIG. 1b shows the displacement of the points of FIG. 1a (illustrated displacement arrows) when the sensor output function is changed for example to $$S_{out,1} = f_1(c_p, c_s, \lambda) = c_p^1 \cdot c_s^1 \cdot \lambda^0$$

(empty symbols before the displacement, filled symbols after the displacement).

In the method according to the present invention, $S_{out}$ is changed in such a way that a group of gases and/or gas mixtures, which shall be referred to hereinafter as gas mixture group, is separated along the sensor output axis completely from the remaining gases and/or gas mixtures of the set, e.g. in the first embodiment by the sensor output function $$S_{out,2} = f_2(c_p, c_s, \lambda) = c_p^1 \cdot c_s^1 \cdot \lambda^0.$$

Figure 2A:
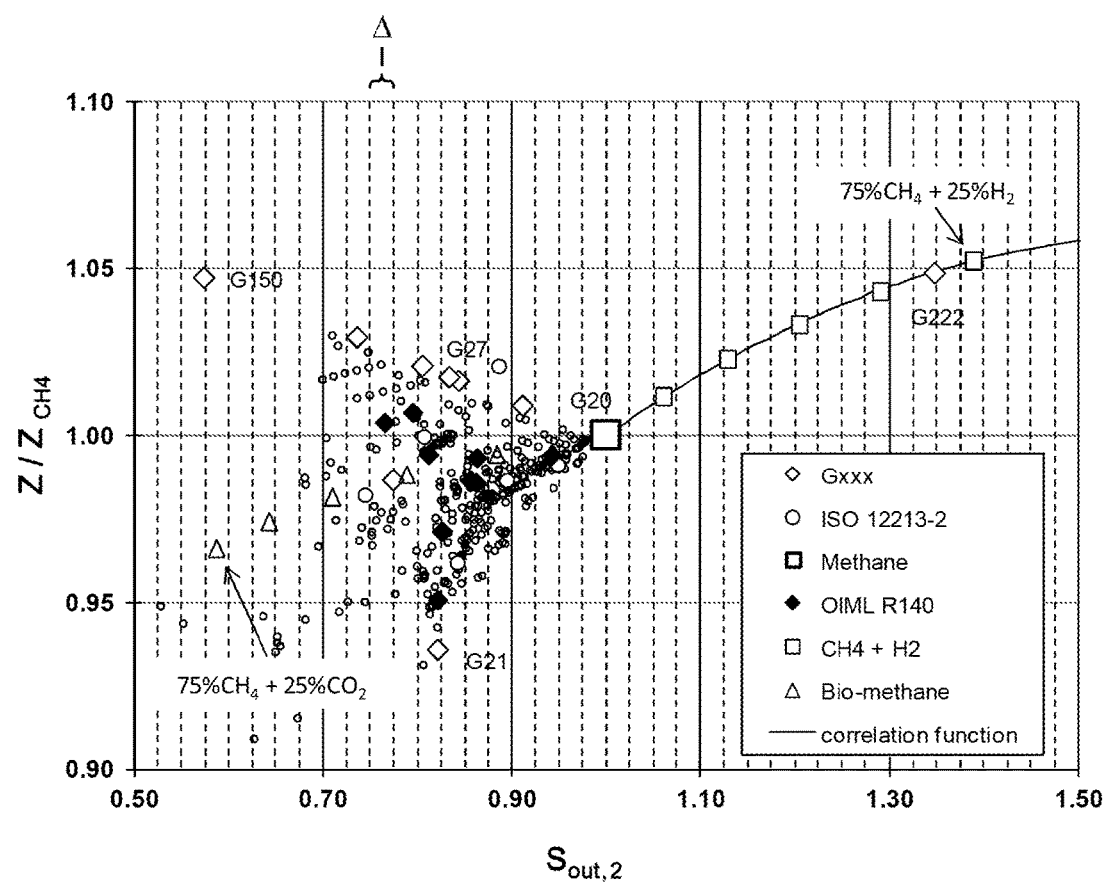
FIG. 2a shows an example for the selection of the output function in the first embodiment for separating hydrogen-rich gases (so-called "hythanes")

FIG. 2a shows an illustration of the compression factor Z depending on $S_{out,2}$ with methane (G20) as the reference. The sensor output $S_{out,2} > 1$ applies to the gas mixture group of the hydrogen-rich gases (so-called "hythanes" of the form $CH_4 + H_2$) which is separated in FIG. 2, and a correlation function can easily be found for this gas mixture group as seen in FIG. 2a, which is why the gas mixture group no longer needs to be considered below.

If the measurement on the other hand produces $S_{out,2} \leq 1$, the H and L gases are for example separated from each other along the $S_{out,3}$ axis in a next step by renewed changing of the sensor output function, e.g. into $$S_{out,3} = f_3(c_p, c_s, \lambda) = c_p^1 \cdot c_s^{-0.5} \cdot \lambda^{-1}.$$

Figure 3:
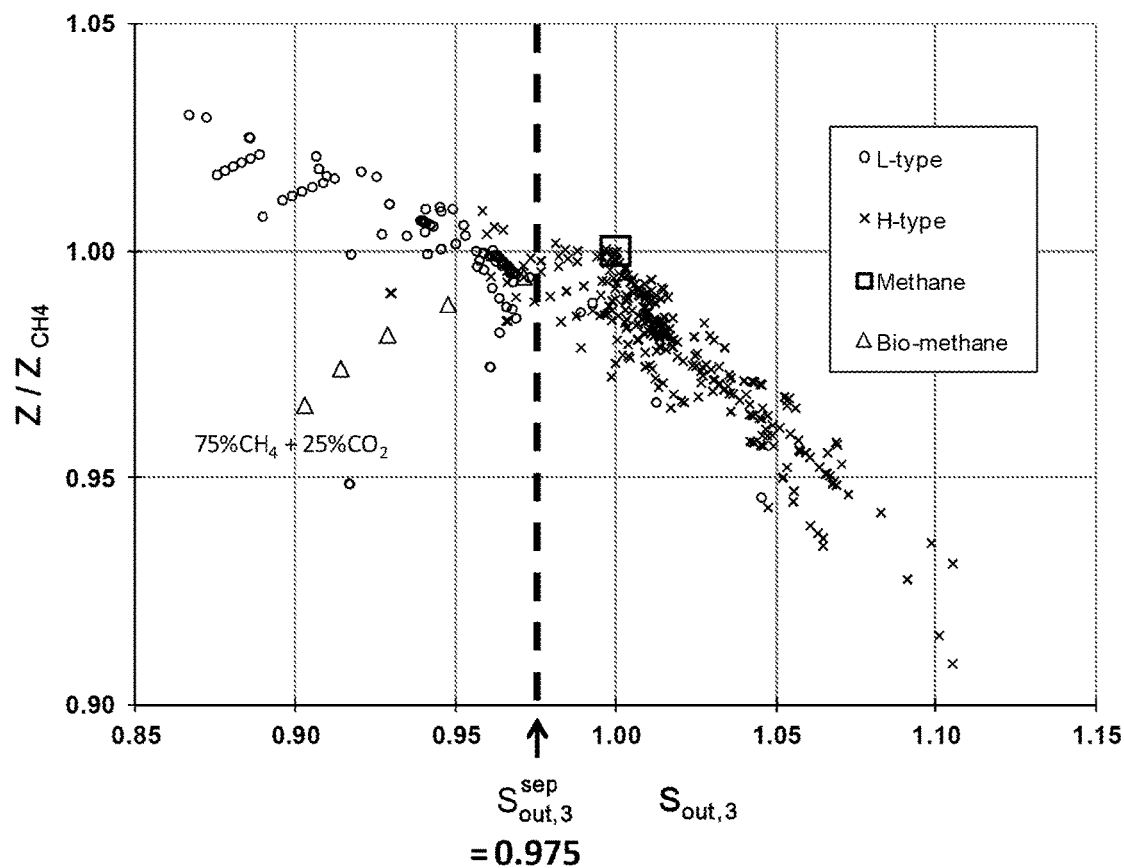
FIG. 3 shows an example for the selection of the sensor output function in the first embodiment for separating H and L gases.

FIG. 3 shows the separation of the H gases from the L gases. If the sensor output $S_{out,3} > 0.975$ applies then an H gas is concerned. An L gas is concerned for $S_{out,3} \leq 0.975$. In the former case, a move is made to the correlation of the compression factor Z for H gases, and in the latter case to the correlation of the compression factor Z for L gases.

Figure 4:
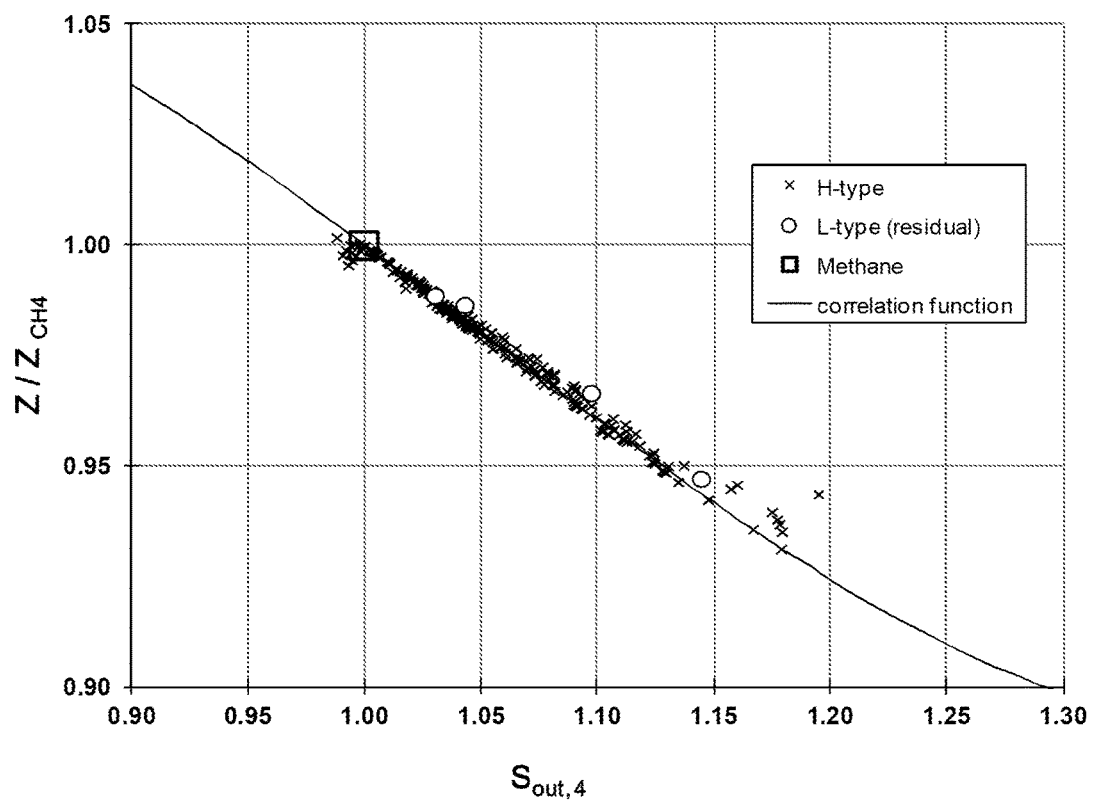
FIG. 4 shows an example for the selection of the sensor output function in the first embodiment for the correlation of the compression factor within the H gases.

The sensor output function $$S_{out,4} = f_4(c_p, c_s, \lambda) = c_p^1 \cdot c_s^{-1} \cdot \lambda^{-1}$$

can be used for the correlation of the compression factor Z for H gases for example. FIG. 4 shows the correlation of the compression factor Z depending on $S_{out,4}$.

Figure 5:
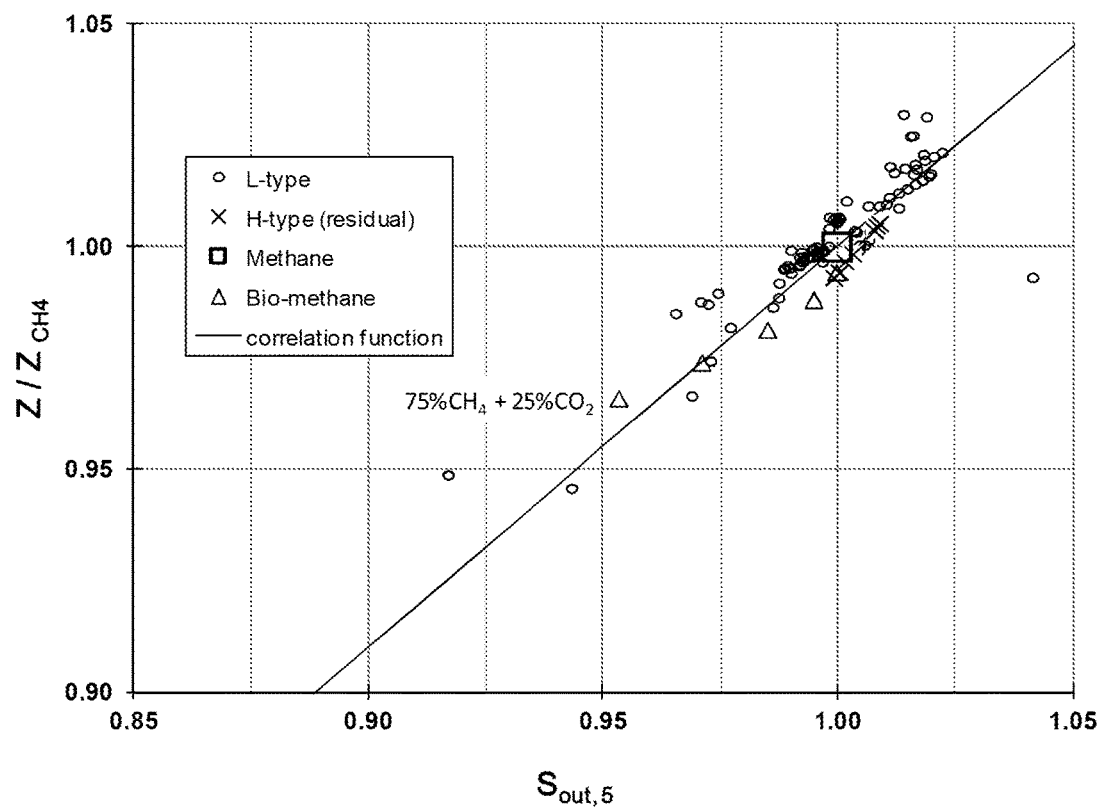
FIG. 5 shows an example for the selection of the sensor output function in the first embodiment for the correlation of the compression factor within the L gases.

The sensor output function $$S_{out,5} = f_5(c_p, c_s, \lambda) = c_p^{0.02} \cdot c_s^{-1.5} \cdot \lambda^2$$

can be used for the correlation of the compression factor Z for L gases for example. FIG. 5 shows the correlation of the compression factor Z depending on $S_{out,5}$.

Figure 2:
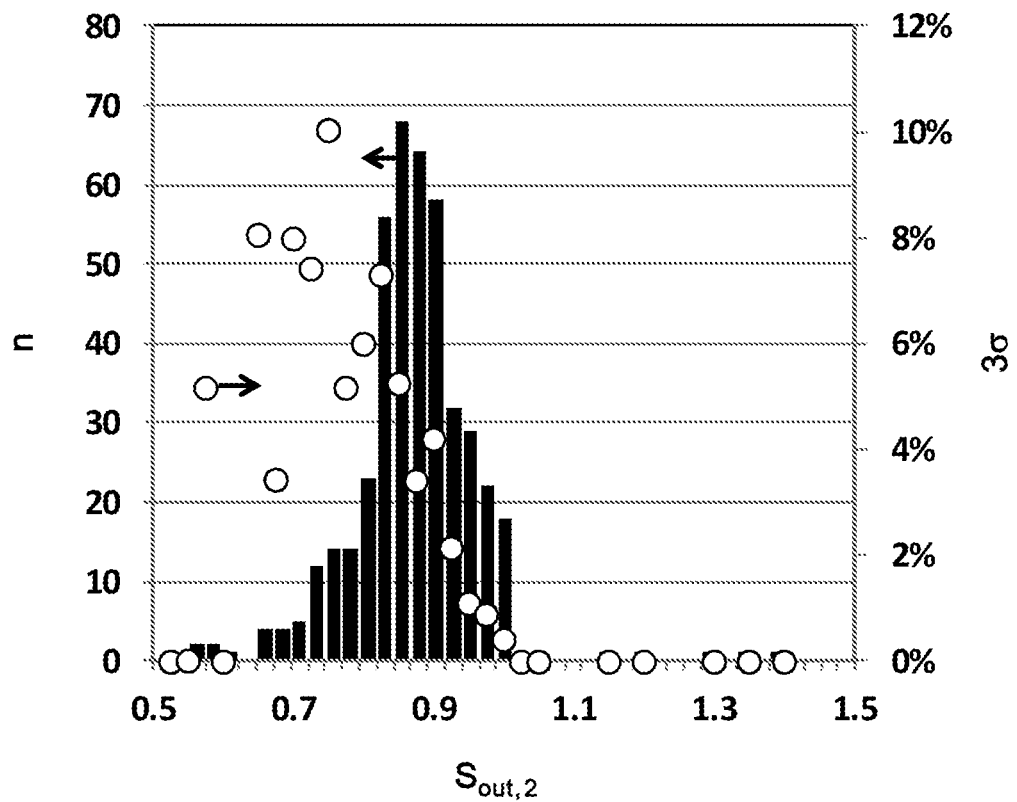

All correlation functions $f_{corr,i}$ of the first embodiment shown in FIGS. 2, 4 and 5 are of the type $$Z = f_{corr,i}(S_{out,i}) = a_{0,i} + a_{1,i} \cdot S_{out,i} + a_{2,i} \cdot S_{out,i}^2 \quad (4),$$

for i=2, 4 and 5, i.e. polynomials of second degree.

Which gas mixture groups can be separated from each other, which sensor output functions $S_{out,i}$ are provided, how many steps are required, and where precisely the separating lines $S_{out,i}^{sep}$ can be drawn depends on the available measuring quantities $\mu_j$ and the gas properties to be determined by correlation. The values mentioned above are merely provided as an example.

In order to illustrate that the method is not limited to the compression factor Z, that the available measuring quantities $\mu_j$ can also be others than heat capacity, sound velocity and thermal conductivity, and that the used sensor output function $S_{out,i}$ or the correlation function $f_{corr,i}$ need not necessarily have the form of the preceding example, the correlation of the Prandtl number Pr shall be presented here in a second, generalising embodiment. Pr is a dimensionless coefficient of fluids named after Ludwig Prandtl, i.e. of gases and liquids, and expresses the ratio of the thickness of the flow boundary layer to the thickness of the thermal boundary layer in heat transfer problems.

Reference is hereby made to the publication EP 2 806 271 A1 concerning the measuring quantities $\mu_j$ in the second embodiment. A method for determining physical properties of gas is described in this publication, in which the gas or gas mixture flows from a gas reservoir under pressure through a critical nozzle and over a microthermal sensor, and the pressure drop in the gas reservoir is measured as a function of time. A first gas property factor $\Gamma^*$ is determined from the pressure drop measurement and a second gas property factor $\Gamma$ is determined from the flow signal of the microthermal sensor.

The first gas property factor $\Gamma^*$ is defined as $$\Gamma^* := C_d \cdot \psi_{max} \cdot \sqrt{\frac{1}{M}}, \qquad (5)$$

wherein $C_d$ designates the "Discharge Coefficient", i.e. the loss factor of a real critical nozzle in relation to an ideal critical nozzle, M the molecular weight of the gas and $\psi_{max}$ the maximum value of the outflow function.

The second gas property factor $\Gamma$ is defined as $$\Gamma = \frac{c_p}{\lambda} \cdot C_d \cdot \psi_{max} \cdot \sqrt{M}, \qquad (6)$$

wherein $c_p$ designates the heat capacity and $\lambda$ the thermal conductivity.

Furthermore, the thermal conductivity $\lambda$ of the gas or gas mixtures is determined with the microthermal sensor and a desired physical gas property is determined from the first and second gas property factor $\Gamma^*$, $\Gamma$ and the thermal conductivity $\lambda$ by correlation.

In the second embodiment, $$S_{out} = f(\Gamma^*, \Gamma, \lambda) = \alpha_1 \cdot (\Gamma^*)^{\beta_1} + \alpha_2 \cdot e^{(\Gamma - \Gamma_0)/\beta_2} + \alpha_3 \cdot \tan h((\lambda - \lambda_0)/\beta_3) \qquad (7)$$

is used as a sensor output function with respectively different constants $\alpha_1$, $\alpha_2$, $\alpha_3$, $\beta_1$, $\beta_2$, $\beta_3$, $\Gamma_0$ and $\lambda_0$.

The correlation function has the following form:

$$Pr = f_{corr}(S_{out}) = a_1 + a_2 \cdot (S_{out} - S_{out,0})^b \qquad (8)$$

i.e. a so-called power function with offset $a_1$, coefficient $a_2$ and exponent b.

Figure 6:
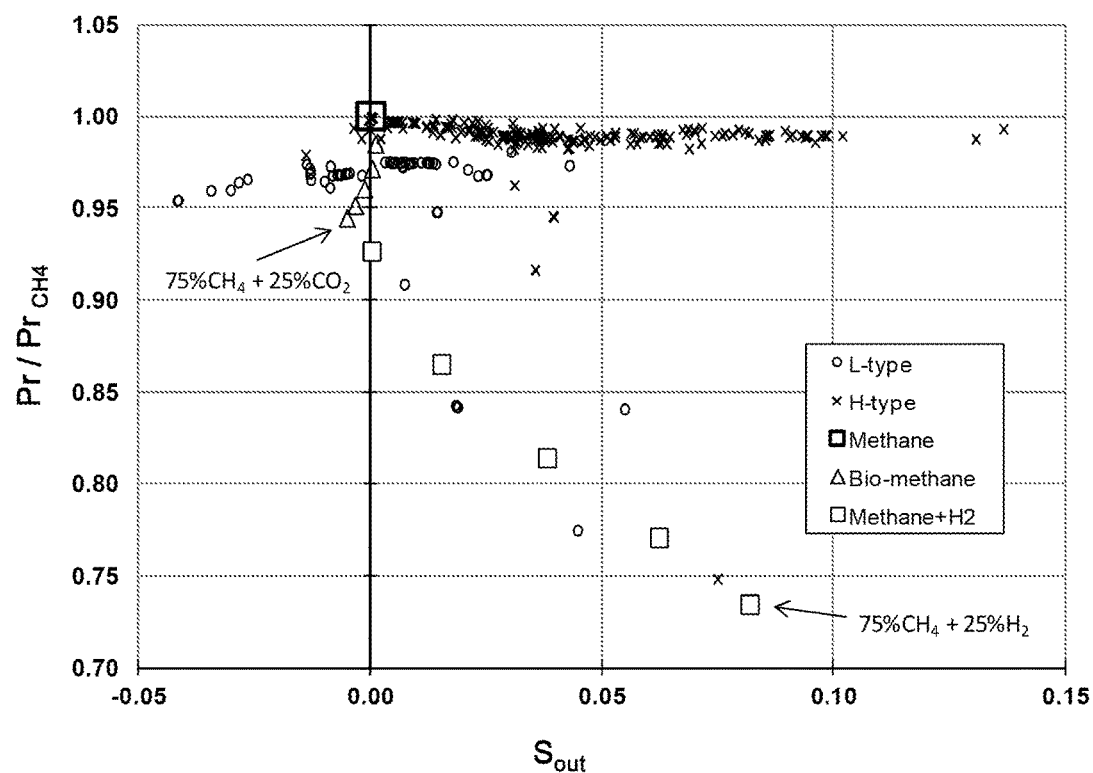
FIG. 6 shows a second embodiment with a graphic representation of the correlation of the Prandtl number according to a method in accordance with the present invention.

It is attempted in a first step of the second embodiment to distinctly map the sensor output $S_{out}$ to the Prandtl number Pr, e.g. by means of the sensor output function (as shown in FIG. 6)

$$S_{out} = \Gamma^* - e^{(\Gamma - 1)} + \tan h(\lambda - 1).$$

Figure 7:
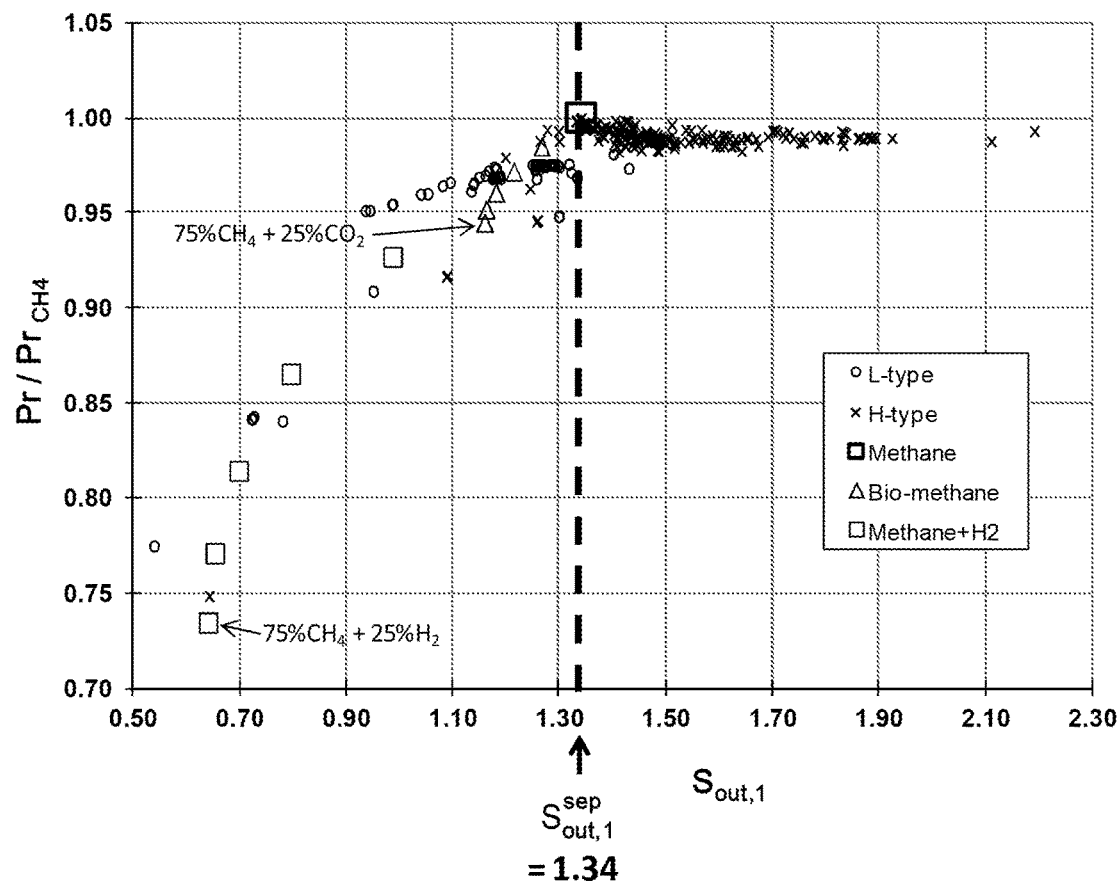
FIG. 7 shows an example for the selection of the sensor output function in the second embodiment for separating the H gases.

If, as shown in FIG. 6, this is not simultaneously possible for all gases and/or gas mixtures of the set, the higher-calorific H gases can be separated in a second step of the method by means of the sensor output function:

$$S_{out,1} = f(\Gamma^*, \Gamma, \lambda) = (\Gamma^*)^5 + 0.125 \cdot e^{(\Gamma - 0.5)/0.5} + 0.125 \cdot \tan h(\lambda - 1)$$

and the limit value $S_{out,1}^{sep} = 1.34$. FIG. 7 shows the separation of the H gases from the remaining gases and gas mixtures.

Figure 8:
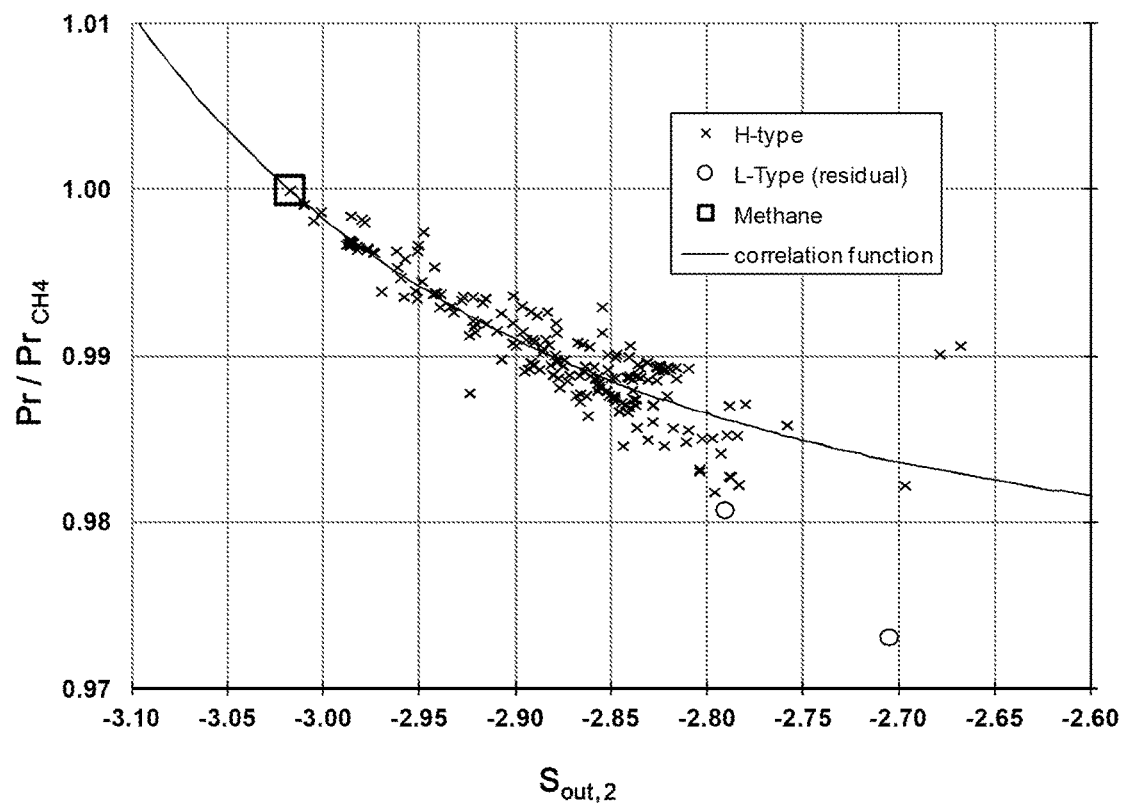
FIG. 8 shows an example for the selection of the sensor output function in the second embodiment for preparing the correlation of the Prandtl number within the H gases.

The correlation of the Prandtl number Pr within the H gases is prepared in a third step of the method by means of $$S_{out,2} = -0.46 \cdot (\Gamma^*)^{3.74} - 0.865 \cdot e^{(\Gamma - 0.25)/0.83} - 2.26 \cdot \tan h((\lambda - 0.73)/1.43)$$

for example, and Pr is determined by means of the correlation function $$Pr = f_{corr}(S_{out,2}) = 0.98 + 0.012 \cdot (S_{out,2} + 3.82)^{-3.37}$$

for example. FIG. 8 shows the correlation of the Prandtl number Pr within the H gases depending on $S_{out,2}$.

The hydrogen-rich gases (so-called "hythanes") are for example separated in a fourth step of the method by means of the sensor output function $$S_{out,3} = f(\Gamma^*, \Gamma, \lambda) = -4.44 \cdot (\Gamma^*)^0 + 2 \cdot e^{(\Gamma - 0.5)/0.5} + \tan h(\lambda - 1)$$

and the limit value $S_{out,3}^{sep} = 0.997$, and the Prandtl number within the hythanes is determined by means of the correlation function $$Pr = f_{corr}(S_{out,3}) = 1.01 \cdot S_{out,3}^{-0.267}.$$

Figure 9:
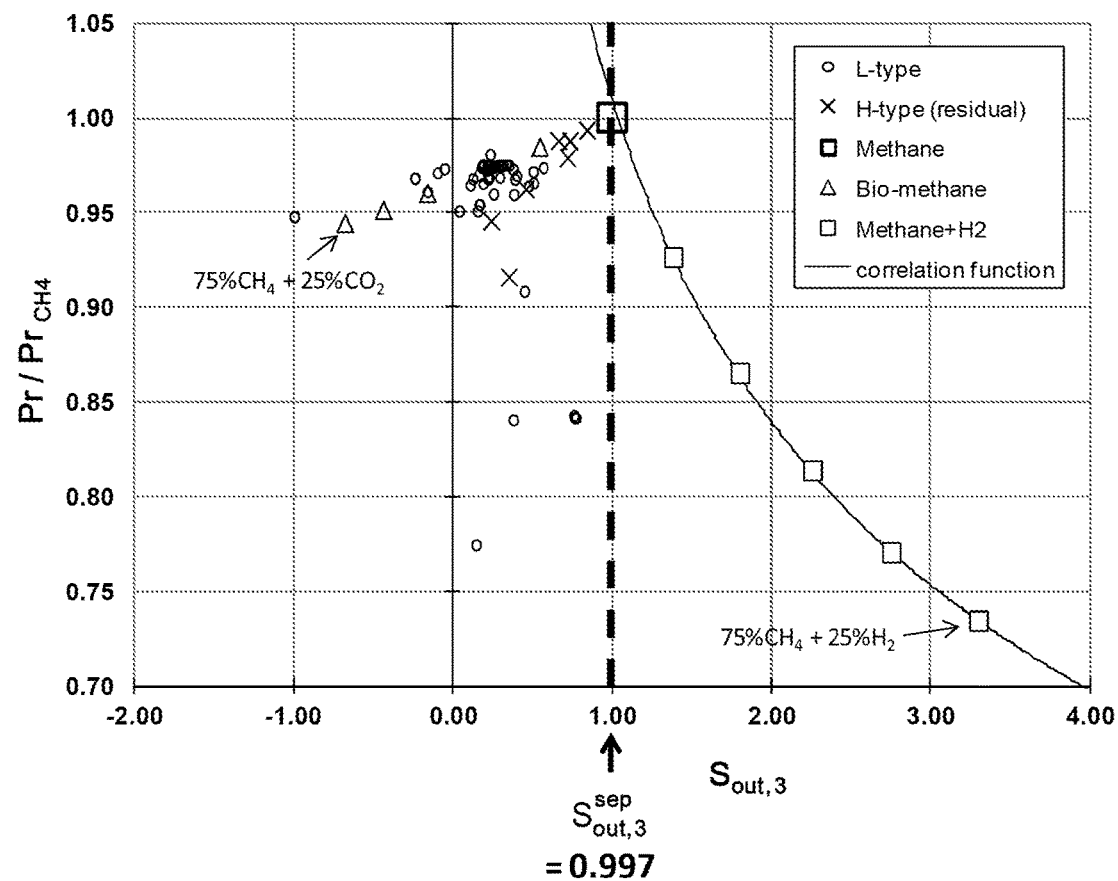
FIG. 9 shows an example for the selection of the sensor output function in the second embodiment for separating hydrogen-rich gases (so-called "hythanes")

FIG. 9 shows the correlation of the Prandtl number Pr within the hythanes depending on $S_{out,3}$.

Figure 10:
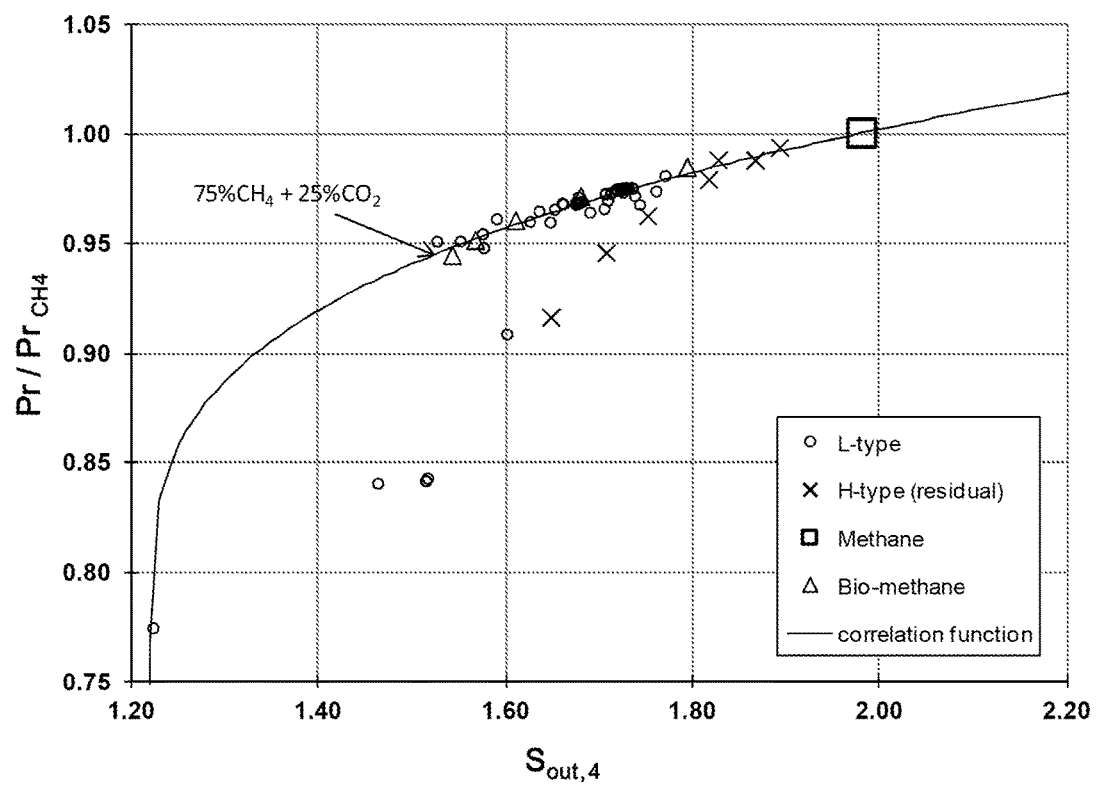
FIG. 10 shows an example for the selection of the sensor output function in the second embodiment for preparing the correlation of the Prandtl number within the L gases.

The correlation of the Prandtl number within the L gases is prepared in a fifth step of the method by means of $$S_{out,4} = f(\Gamma^*, \Gamma, \lambda) = (\Gamma^*)^2 + 0.5 \cdot e^{(\Gamma - 1)/0.1} + 0.5 \cdot \tan h(\lambda + 1)$$

for example, and Pr is determined by means of the correlation function $$Pr = f_{corr}(S_{out,4}) = 0.77 + 0.25 \cdot (S_{out,4} - 1.22)^{0.3}$$

for example. FIG. 10 shows the correlation of the Prandtl number Pr within the L gases depending on $S_{out,4}$.

Figure 11:
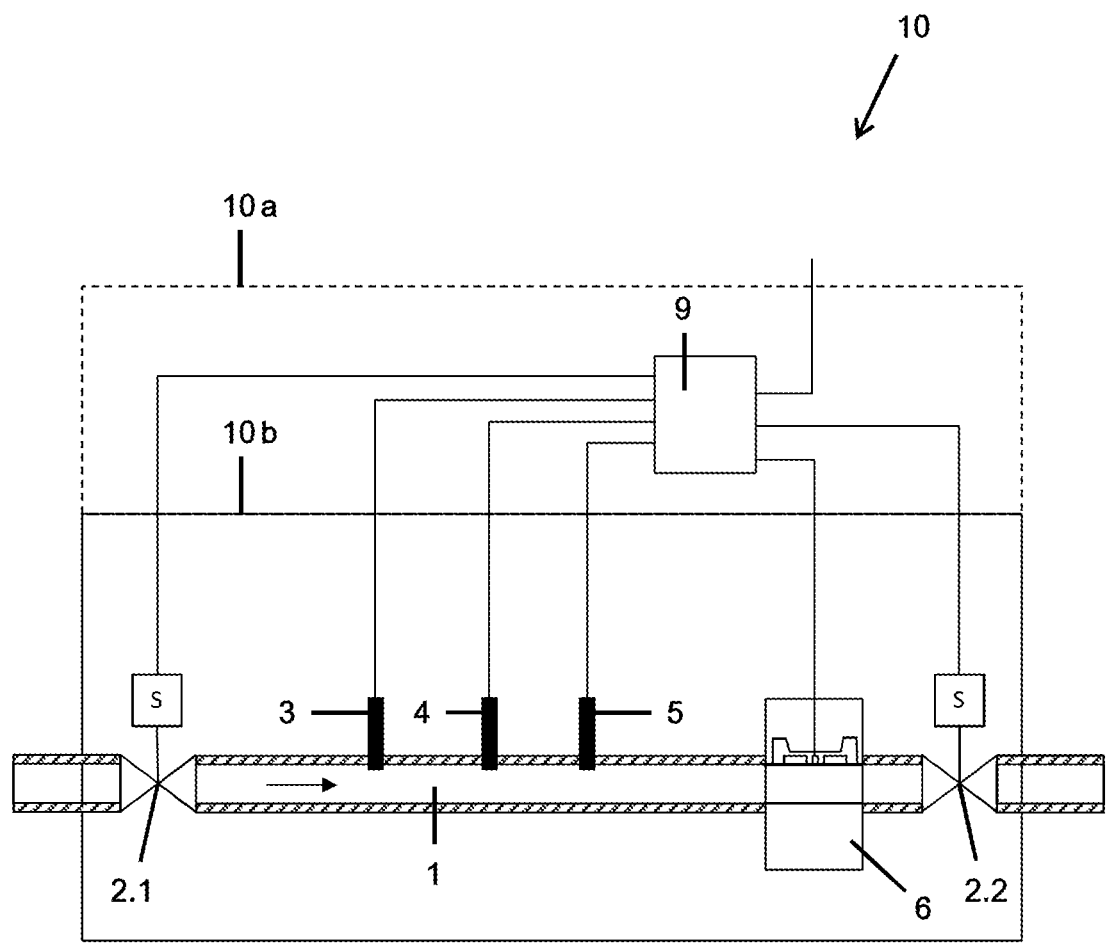
FIG. 11 shows an embodiment of the schematic configuration of a measuring apparatus according to the present invention.

FIG. 11 shows an embodiment of the schematic configuration of a measuring apparatus according to the present invention. In the embodiment, the measuring apparatus 10 comprises one or several sensors 3, 4, 5, 6 for detecting physical measuring quantities $\mu_j$ (j=1, . . . , m) and an evaluation unit 9 which is configured for carrying out a method according to the present invention or one of the aforementioned embodiments or variants of the method. One or several of the following sensors can be provided as sensors: a microthermal sensor 6, an ultrasonic flow sensor 5, a temperature sensor 4, a pressure sensor 3 or any other matching sensor. The sensors are arranged in a gas line 1 in an advantageous embodiment.

Some or all of these components can be combined into an assembly, wherein the evaluation unit 9 can be a component of said assembly (variant 10a), or the evaluation unit can be added separately (variant 10b), e.g. in a superordinate computing unit.

If necessary, the measuring apparatus 10 can contain additional components such as one or several shut-off valves 2.1, 2.2. It is possible by means of the shut-off valves to detect one or several of the physical measuring quantities selectively under flow or no-flow conditions.

The aforementioned method and the aforementioned embodiments and variants as well as the aforementioned measuring apparatus are suitable for example for determining gas properties of combustible gases and/or gas mixtures and/or gases and/or gas mixtures from the energy sector.

The method and the measuring apparatus according to the present invention offer the advantage that due to the correlation in several steps the precision of the determination of gas properties from measured physical values of the gases and/or gas mixtures can be improved, and the quantity of the gases and/or gas mixtures for which the method can be applied with the desired precision is greater than in simple correlation methods. It is a further advantage that the presented measuring apparatus can be produced at comparatively low cost, which allows an economical on site determination of gas properties.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for the determination of gas properties by correlation in which a gas property (Q) is determined by correlation from physical measuring quantities ($\mu_j$ (j=1, ..., m)) of the gases and/or gas mixtures, and the method comprises:
   combining the physical measuring quantities ($\mu_j$ (j=1, ..., m)) into a sensor output ($S_{out}=f(\mu_1, ..., \mu_m)$) by making use of a sensor output function (f),
   comparing the sensor output ($S_{out}$) with a limit value ($S_{out}^{sep}$) in order to determine whether the sensor output, within a set (G) of gases and/or gas mixtures to which the method is applied, belongs to a group of gases and/or gas mixtures which is referred to below as gas mixture group (GG), in which a correlation between the sensor output ($S_{out}$) and the gas property (Q) to be determined is better than in the entire set (G), and
   if the sensor output ($S_{out}$) belongs to the gas mixture group (GG), the gas property (Q) is determined from the sensor output with a correlation function ($f_{corr}$) which is specific to the gas mixture group.

2. The method according to claim 1, wherein the affiliation with a gas mixture group is checked in two, three, four or more steps,
   in that the physical measuring quantities ($\mu_j$ (j=1, ..., m)) are combined into a further sensor output ($S_{out,i}=f_i(\mu_1, ..., \mu_m)$) respectively by making use of a sensor output function ($f_i$) which is specific to the gases and/or gas mixtures ($G_{rest,i}$) of the set that have remained after the separation of the preceding gas mixture group or groups, which are referred to below as the remaining gases and/or gas mixtures ($G_{rest,i}$), and the further sensor output ($S_{out,i}$) is compared with a further limit value ($S_{out,i}^{sep}$) in order to determine whether the further sensor output belongs within the remaining gases and/or gas mixtures ($G_{rest,i}$) to a further gas mixture group ($GG_i$) in which the correlation between the further sensor output ($S_{out,i}$) and the gas property (Q) to be determined is better than within the remaining gases and/or gas mixtures ($G_{rest,i}$), and
   if the further sensor output ($S_{out,i}$) belongs to the further gas mixture group ($GG_i$), the gas property (Q) is determined from the further sensor output with a correlation function ($f_{corr,i}$) which is specific to the further gas mixture group.

3. The method according to claim 1, wherein, if the sensor output ($S_{out}$, $S_{out,i}$) does not belong to one of the gas mixture groups (GG, $GG_i$), the gas property (Q) is determined from the sensor output with a correlation function ($f_{corr,i}$) which is specific to the remaining gases and/or gas mixtures ($G_{rest}$, $G_{rest,i}$).

4. The method according to claim 1, wherein the sensor output ($S_{out}$, $S_{out,i}$) is changed before the correlation with a further sensor output function ($f_i$) in order to prepare the correlation between the sensor output (S) and the gas property (Q).

5. The method according to claim 1, wherein the sensor output function (f) and a limit value ($S_{out}^{sep}$) for the sensor output are determined in such a way that a gas mixture group (GG) is separated by the limit value from a set (G) of gases and/or gas mixtures for which the gas property (Q) is determined, within which the correlation between the sensor output ($S_{out}$) and the desired gas property (Q) is better than in the entire set (G).

6. The method according to claim 1, wherein the relationship $$S_{out}^{GG} < S_{out}^{sep}$$

applies to the gases and/or gas mixtures of the gas mixture group (GG), and the relationship $$S_{out}^{Grest} \geq S_{out}^{sep},$$

applies to the remaining gases and/or gas mixtures (Guest) of the set,
   or from case to case, instead of the aforementioned relationships, the relationships $S_{out}^{GG} > S_{out}^{sep}$ and $S_{out}^{Grest} \leq S_{out}^{sep}$ apply.

7. The method according to claim 1 wherein the steps are carried out automatically.

8. The method according to claim 1, wherein the sensor output function or sensor output functions (f, $f_i$) and/or the limit value or values ($S_{out}^{sep}$, $S_{out,i}^{sep}$) for the sensor output and/or the correlation functions ($f_{corr}$, $f_{corr,i}$) are determined in advance, e.g. on the basis of values of the physical measuring quantities and the gas property to be determined from tables and/or technical literature and/or databases and/or measurements.

9. The method according to claim 1, wherein the sensor output function or the sensor output functions (f, $f_i$) and/or the limit value or values ($S_{out}^{sep}$, $S_{out,i}^{sep}$) for the sensor output are determined by a computer program in that:
   for each function ($f_i$) in a set of possible sensor output functions the respective functional parameters ($p_{fi}$) of ($f_i$) such as polynomial coefficients, exponents or constants, are varied within preset limit values for ($p_{fi}$), e.g. by means of a Monte Carlo selection method,
   the sensor output range is subdivided into intervals and the number of ambiguities is counted in particular in each interval, i.e. the number of events for which two or more gas mixtures show different values for the quantity (Q) to be determined or the values for the quantity (Q) to be determined lie outside of a preset value interval for (Q),
   the function ($f_i$) and the specific functional parameter set ($p_{fi}$) are determined for which the fewest of such ambiguity events occur, or the variance ($3\sigma$) of the values for the quantity (Q) to be determined is minimal in case of ambiguity events in an interval, or a preset maximum permitted number ($n_{max}$) of the ambiguity events or a preset maximum permitted variance ($3\sigma_{max}$) of the Q values is not exceeded in case of ambiguity events in an interval, and
   in that it is determined in particular from which limit value ($S_{out,i}^{sep}$) a number ($n_{max}$) of the ambiguity events preset for each interval for the determination of the limit value or a variance ($3\sigma_{max}$) of the Q values preset for each interval for the determination of the limit value is not exceeded in case of ambiguity events.

10. The method according to claim 1, wherein at least two or all correlation functions differ from each other, and/or wherein the points of the gases and/or gas mixtures of the gas mixture group or groups each lie on a line described by a distinct correlation function or in tolerance ranges which adjoin such a line on both sides, and which for example are not greater than 0.25% or 0.75% or 2% of the value of the gas property (Q).

11. The method according to claim 1, wherein the sensor output function ($f$) or sensor output functions ($f_i$) are of the type $$S_{out,i} = \mu_1^{p_{1,i}} \cdot \ldots \cdot \mu_m^{p_{m,i}}$$

and $p_{1,i}, \ldots, p_{m,i}$ are exponents, and/or wherein the correlation function ($f_{corr}(S_{out})$) or correlation functions ($f_{corr,i}(S_{out,i})$) are of the type $$Q = f_{corr,i}(S_{out,i}) = a_{0,i} + a_{1,i} \cdot S_{out,i} + a_{2,i} \cdot S_{out,i}^2$$

and $a_{0,i}$, $a_{1,i}$ and $a_{2,i}$ are constants.

12. The method according to claim 1, wherein the Pearson correlation coefficient ($Kor(S_{out}, Q)$) is used as a measure for the precision of the correlation, and wherein a better correlation means that the Pearson correlation coefficient lies closer to the value 1 or −1, in particular that the absolute value of the difference from the value 1 or −1 is less than 0.3 or 0.2 or 0.1.

13. The method according to claim 1, wherein the physical measuring quantities ($\mu_j$ (j=1, ..., m)) are detected with one or several sensors, and/or wherein at least two of the measuring quantities thermal conductivity, heat capacity, thermal diffusivity, density, flow velocity, mass flow, sound velocity, dielectric constant, viscosity, infrared absorption, pressure or temperature are detected as physical measuring quantities ($\mu_j$ (j=1, ..., m)).

14. A measuring apparatus for determining gas properties with one or several sensors for detecting physical measuring quantities ($\mu_j$ (j=1, ..., m)) and with an evaluation unit which is set up for carrying out a method according to claim 1.

15. The measuring apparatus according to claim 14, wherein the evaluation unit forms an assembly together with the sensor or sensors, or wherein the evaluation unit is formed in a separate or superordinate computing unit.

16. A method to determine gas properties comprising:
measuring physical quantities ($\mu_j$ (j=1, ..., m)) of a gas or gas mixture with a sensor;
generating a sensor output ($S_{out} = f(\mu_1, \ldots, \mu_m)$) representative of a combination of the measured physical quantities;
comparing the sensor output ($S_{out} = f(\mu_1, \ldots, \mu_m)$) to a limit value ($S_{out}^{sep}$);
based on the comparison, determining whether the sensor output ($S_{out} = f(\mu_1, \ldots, \mu_m)$) corresponds to a gas mixture group (GG), and
if the sensor output ($S_{out} = f(\mu_1, \ldots, \mu_m)$) corresponds to the gas mixture group (GG), determining a gas property (Q) for the gas or gas mixture from the sensor output ($S_{out} = f(\mu_1, \ldots, \mu_m)$) and using a correlation function ($f_{corr}$) which is specific to the gas mixture group (GG).

* * * * *

UNITED STATES PATENT AND TRADEMARK OFFICE
CERTIFICATE OF CORRECTION

PATENT NO. : 10,371,678 B2
APPLICATION NO. : 15/379003
DATED : August 6, 2019
INVENTOR(S) : Pretre et al.

Page 1 of 2

It is certified that error appears in the above-identified patent and that said Letters Patent is hereby corrected as shown below:

In the Specification

Column 4, Line 17, "further gas mixture group GG" should read --further gas mixture group $GG_i$,--.

Column 8, Line 14, " $S_{out,2} = f_2(c_p, c_s, \lambda) = c_p^1 \cdot c_s^1 \cdot \lambda^0$." should read --$S_{out,2} = f_2(c_p, c_s, \lambda) = c_p^1 \cdot c_s^1 \cdot \lambda^0$.--.

Column 9, Lines 41-42, " $S_{out} = f(\Gamma^*, \Gamma, \lambda) = \alpha_1 \cdot (\Gamma^*)^{\beta_1} + \alpha_2 \cdot e^{(\Gamma-\Gamma_0)/\beta_2} + \alpha_3 \cdot \tan h((\lambda - \lambda_0)/\beta_3)$ "
should read --$S_{out} = f(\Gamma^*, \Gamma, \lambda) = \alpha_1 \cdot (\Gamma^*)^{\beta_1} + \alpha_2 \cdot e^{(\Gamma-\Gamma_0)/\beta_2} + \alpha_3 \cdot \tanh((\lambda - \lambda_0)/\beta_3)$--.

Column 9, Line 55, "$S_{out} = \Gamma^* - e^{(\Gamma-1)} + \tan h(\lambda-1)$" should read --$S_{out} = \Gamma^* - e^{(\Gamma-1)} + \tanh(\lambda - 1)$--.

Column 9, Lines 61-62 " $S_{out,1} = f(\Gamma^*, \Gamma, \lambda) = (\Gamma^*)^5 + 0.125 \cdot e^{(\Gamma-0.5)/0.5} + 0.125 \cdot \tan h(\lambda-1)$ " should read
--$S_{out,1} = f(\Gamma^*, \Gamma, \lambda) = (\Gamma^*)^5 + 0.125 \cdot e^{(\Gamma-0.5)/0.5} + 0.125 \cdot \tanh(\lambda - 1)$--.

Column 10, Lines 1-2, " $S_{out,2} = -0.46 \cdot (\Gamma^*)^{3.74} - 0.865 \cdot e^{(\Gamma-0.25)/0.83} - 2.26 \cdot \tan h((\lambda-0.73)/1.43)$ " should read
--$S_{out,2} = -0.46 \cdot (\Gamma^*)^{3.74} - 0.865 \cdot e^{(\Gamma-0.25)/0.83} - 2.26 \cdot \tanh((\lambda - 0.73)/1.43)$--.

Signed and Sealed this
Third Day of March, 2020

Andrei Iancu
*Director of the United States Patent and Trademark Office*

CERTIFICATE OF CORRECTION (continued)

Column 10, Lines 13-14, "$S_{out,3} = f(\Gamma^*,\Gamma,\lambda) = -4.44 \cdot (\Gamma^*)^0 + 2 \cdot e^{(\Gamma-0.5)/0.5} + \tan h(\lambda-1)$" should read -- $S_{out,3} = f(\Gamma^*, \Gamma, \lambda) = -4.44 \cdot (\Gamma^*)^0 + 2 \cdot e^{(\Gamma-0.5)/0.5} + \tanh(\lambda - 1)$ --.

Column 10, Line 25, "$S_{out,4} = f(\Gamma^*,\Gamma,\lambda) = (\Gamma^*)^2 + 0.5 \cdot e^{(\Gamma-1)/0.1} + 0.5 \cdot \tan h(\lambda+1)$" should read -- $S_{out,4} = f(\Gamma^*, \Gamma, \lambda) = (\Gamma^*)^2 + 0.5 \cdot e^{(\Gamma-1)/0.1} + 0.5 \cdot \tanh(\lambda + 1)$ --.

In the Claims

Claim 4, Column 12, Line 8, "sensor output (S)" should read --sensor output ($S_{out,i}$)--.

Claim 6, Column 12, Line 27, "(Guest)" should read --($G_{rest}$)--.

Claim 16, Column 14, Line 30, "($S_{out}$f($\mu_1$, ..., $\mu_m$))" should read --($S_{out}$ = f ($\mu_1$,...,$\mu_m$))--.